United States Patent [19]

Kim et al.

[11] Patent Number: 5,177,012
[45] Date of Patent: Jan. 5, 1993

[54] BIOSENSOR CONTAINING IMMOBILIZED ZYMOMONAS MOBILIS CELLS FOR MEASURING GLUCOSE, FRUCTOSE AND SUCROSE

[75] Inventors: Hak-Sung Kim; Je-Kyun Park, both of Seoul, Rep. of Korea

[73] Assignee: Korea Advanced Institute of Science & Technology, Seoul, Rep. of Korea

[21] Appl. No.: 572,254

[22] Filed: Aug. 27, 1990

[30] Foreign Application Priority Data

Oct. 25, 1989 [KR] Rep. of Korea .................... 89-15344

[51] Int. Cl.⁵ ..................... C12N 11/18; C12N 11/02; C12M 1/40
[52] U.S. Cl. .................................... 435/175; 204/403; 435/14; 435/177; 435/178; 435/180; 435/182; 435/288; 435/817
[58] Field of Search ....................... 435/14, 174, 175, , 435/177, 178, 180, 181, 182, 817; 204/403

[56] References Cited

U.S. PATENT DOCUMENTS

| | | | |
|---|---|---|---|
| 4,350,765 | 9/1982 | Chibata et al. | 435/182 X |
| 4,459,312 | 7/1984 | Hartmeier | 435/175 X |
| 4,755,467 | 7/1988 | Scopes et al. | 435/158 X |
| 5,017,485 | 5/1991 | Bringer-Meyer et al. | 435/158 |

OTHER PUBLICATIONS

Kobos, R. K., Trends in Analytical Chemistry, vol. 2, No. 7, 1983, pp. 154–157.
Hans Nilsson et al., "Determination of Glucose Urea and Penicillin Using Enzyme-PH Electrode," Biochimica et Biophysice Acta, 320 (1973), pp. 529–534.
Ikuo Satoh, et al., "Enzyme Electrode for Sucrose," Biotechnology and Bioengineering, vol. XVIII (1976), pp. 269–272.
Jean-Louis Romette et al., "Glucose-Oxidase Electrode, Measurement of Glucose in Samples Exhibiting High Variability in Oxygen Content," Clinica Chimica Acta, 95 (1979), pp. 249–253.

Primary Examiner—David M. Naff
Attorney, Agent, or Firm—Oblon, Spivak, McClelland, Maier & Neustadt

[57] ABSTRACT

A biosensor for the determination of glucose and fructose concentrations is provided. The biosensor is produced by a method which comprises treating Zymomonas mobilis whole cells with an organic solvent such as xylene and n-butanol, immobilizing the treated whole cells onto a support selected from the group consisting of gelatin, collagen, agarose, cellophane and polyacrylamide to give an immobilized whole cell enzyme membrane and adhering the membrane to the surface of a pH electrode to give the biosensor. The resulting biosensor is capable of determning glucose and fructose in high concentrations such as 5 g/L and 50 g/L, respectively. Invertase can be immobilized with the whole cells to provide a biosensor for the determination of sucrose.

7 Claims, No Drawings

BIOSENSOR CONTAINING IMMOBILIZED *ZYMOMONAS MOBILIS* CELLS FOR MEASURING GLUCOSE, FRUCTOSE AND SUCROSE

BACKGROUND OF THE INVENTION

1. Field of the Invention

The present invention relates to a process for the production of a biosensor for the measurement of glucose and fructose concentrations by means of whole cell enzymes of a microorganism.

More specifically, the present invention relates to a process for the production of a biosensor, which comprises treating cells of *Zymomonas mobilis* with an organic solvent and immobilizing the whole cells onto an immobilizing support selected from the group consisting of gelatin, collagen, agarose, cellophane and polyacrylamide to give immobilized whole cell enzyme membranes and then adhering the membranes to the surface of a pH electrode.

The biosensor according to the present invention is valuable for use in determining glucose and fructose concentrations up to 5 g/L and 50 g/L, respectively.

2. Description of the Prior Art

Hitherto, a number of biosensors for the measurement of glucose concentration has been developed. Most of these biosensors employ either an oxygen electrode or ion-selective electrode as the electrode.

However, the conventional biosensors have not been widely used because when purified enzymes are used, their stability is not satisfactory. On the other hand, when immobilized whole cells are used, their selectivity and reaction response are lower than when the purified enzymes are used. Further, the conventional biosensors have a limitation on measurement ranges and suffer from the disadvantage that it is not capable of determining high concentrations of the sample in a direct manner.

SUMMARY OF THE INVENTION

The object of the present invention is to provide a biosensor capable of determining glucose and fructose even in high concentrations by utilizing whole cell enzymes of the microorganisms which have high selectivity and sensitivity.

This and other objects of the invention can be achieved by treating whole cells of *Zymomonas mobilis* with an organic solvent, immobilizing the whole cells onto an immobilizing support which is selected from the group consisting of gelatin, collagen, agarose, cellophane and polyacrylamide to give immobilized whole cell enzyme membranes and then adhering the membranes to the surface of a pH electrode to give a biosensor.

DETAILED DESCRIPTION OF THE INVENTION

The present invention is based on the fact that glucose and fructose in mixture are converted to gluconic acid and sorbitol under the action of glucose-fructose oxidoreductase and gluconolactonase. When the quantity of either glucose or fructose is fixed at a constant value, gluconic acid is formed in proportion to the level of the other substance present in a sample solution. At this time, the variation in hydrogen-ion concentrations is determined by means of the pH electrode.

It has been reported that the glucose-fructose oxidoreductase requires NADP(H) as a coenzyme, and this coenzyme is regenerated by itself through a redox-reaction of enzyme because it is firmly bound to an active site of enzyme.

According to the present invention, whole cells are treated with an organic solvent such as xylene and n-butanol, and the treated cells are immobilized onto an immobilizing support to give immobilized whole cell enzyme membranes, which are then made adhered onto the surface of a pH electrode by means of a nylon net and a silicon O-ring to give a biosensor.

The immobilizing support may be selected from the group consisting of gelatin, collagen, agarose, cellophane and polyacrylamide. Gelatin is preferred because it is easily available.

The biosensor is then installed inside the flow cell equipped with an inlet and an outlet for sample and buffer solutions and maintained at 39° C. A pH-meter and a microcomputer are connected to the measuring equipment, and the initial rate in change of hydrogen-ion concentrations in the immobilized whole cell enzyme membranes is automatically recorded.

With the use of the biosensor of the invention, the sample analysis is complete within 2 minutes. Once the measurement is complete, a MES buffer solution is passed inside the flow cell by an aid of a pump for the next analysis of the sample. The standard calibration curve for the measurement of glucose and fructose concentrations can be obtained by the use of the above method. The present method is capable of determining glucose in concentrations up to 5 g/L, and fructose up to 50 g/L.

The biosensor which is produced by immobilizing the above mentioned whole cell enzymes along with an invertase can be also used for the determination of sucrose concentrations. In this case, glucose and fructose which are formed in equal amounts by the invertase are utilized in the determination of the sucrose level.

DESCRIPTION OF THE PREFERRED EMBODIMENTS

Example 1

Pretreatment of Whole Cells

Whole cells obtained from an culture medium of *Zymomonas mobilis* were mixed with xylene [or n-butanol] for 5 to 10 minutes. The mixture was separated by centrifugation, and the supernatant was discarded. The whole cell sediment was washed twice with a MES buffer solution (pH 6.2) to obtain whole cell enzymes of the microorganism.

Example 2

Preparation of Membranes Containing whole Cell Enzymes.

The whole cell enzymes of the microorganism obtained in Example 1 were mixed with a 10% (w/v) gelatin solution in a ratio of 1:1 (v/v) at ambient temperature. The mixture was evenly spread onto a glass plate over an area of 200 cm² and then dried for 2 hrs. to give a membrane. After the membrane was activated by pouring distilled water over it, the swelled membrane was peeled off from the plate by a razor blade and immersed in a solution of glutaraldehyde for some time. Thereafter, the membrane was washed with distilled water and stored in a MES buffer solution at 4° C. The produced whole cell enzyme membrane was about 100 μm in thickness and maintained in an even state.

The same enzyme membranes were obtained by using collagen, agarose, cellophane or polyacrylamide instead of gelatin.

Example 3

Electrode Having Whole Cell Enzyme Membrane

The membrane obtained in Example 2 was cut off to a piece of about 2 cm$^2$ in size and it was adhered onto the surface of a pH electrode by means of a nylon net and a silicon O-ring (diameter: 10 mm). The electrode was installed inside a flow cell maintained at 39° C. The sample solution was injected into a lower portion of the flow cell by a micro-syringe.

Example 4

Analysis of Samples

The biosensor produced in Example 3 was first immersed in a MES buffer solution for a sufficient time, and then was used for the analysis. After 100 μl of a sample solution was injected through an inlet of the flow cell by a micro-syringe, the output from the biosensor was digitalized, which was subjected to a repeated analysis to determine automatically the initial reaction rate by an aid of a computer.

After the analysis was complete, the buffer solution was fed to the flow cell and then used for a next analysis.

Example 5

Determination of Concentration of Glucose

For the determination of glucose concentrations, the same procedures as in Example 4 were repeated, except that concentrations of glucose varied, while fixing the concentration of fructose at 30 g/L or 50 g/L. The method was capable of determining glucose in concentrations up to 5 g/L.

Example 6

Determination of Concentrations of Fructose

The same procedures as in Examples 4 and 5 were repeated, except that concentrations of fructose varied, while fixing the concentration of glucose at 30 g/L or 50 g/L. The method was capable of determining fructose in concentrations up to 50 g/L.

What is claimed is:

1. A process for the production of a biosensor for measuring glucose and fructose which comprises treating *Zymomonas mobilis* whole cells with an organic solvent, immobilizing the treated whole cells onto a support selected from the group consisting of gelatin, collagen, agarose, cellophane and polyacrylamide to give an immobilized whole cell enzyme membrane, and adhering the membrane to the surface of a pH electrode to give the biosensor.

2. The process of claim 1, in which said organic solvent is xylene or n-butanol.

3. The process of claim 1, in which an invertase is further immobilized concurrently with the whole cells treated with the organic solvent.

4. The process of claim 3, in which the biosensor produced is used for the determination of sucrose concentration.

5. A biosensor for measuring glucose and fructose comprising:
a) an immobilized whole cell enzyme membrane; and
b) a pH electrode,
said membrane being adhered to the surface of said pH electrode and comprising *Zymomonas mobilis* whole cells which have been permeabilized with an organic solvent and then immobilized onto a support selected from the group consisting of gelatin, collagen, agarose, cellophane and polyacrylamide.

6. The biosensor of claim 5, wherein said membrane further comprises an invertase co-immobilized with the whole cells.

7. The biosensor of claim 6, wherein said biosensor is a biosensor for measuring sucrose concentration.

* * * * *